US009763873B2

(12) United States Patent
Stangl et al.

(10) Patent No.: US 9,763,873 B2
(45) Date of Patent: Sep. 19, 2017

(54) PREPARATION FOR PROTECTING AGAINST EXTRINSIC AND INTRINSIC SKIN AGING

(71) Applicant: La Prairie Group AG, Volketswil/Zurich (CH)

(72) Inventors: Daniel Stangl, Meggen (CH); Bernhard Dudler, Hinwil (CH)

(73) Assignee: LA PRAIRIE GROUP AG, Zurich (CH)

( * ) Notice: Subject to any disclaimer, the term of this patent is extended or adjusted under 35 U.S.C. 154(b) by 217 days.

(21) Appl. No.: 14/453,822

(22) Filed: Aug. 7, 2014

(65) Prior Publication Data
US 2015/0050316 A1    Feb. 19, 2015

(30) Foreign Application Priority Data

Aug. 16, 2013   (DE) .................. 10 2013 216 295

(51) Int. Cl.
| | |
|---|---|
| *A61K 36/185* | (2006.01) |
| *A61K 36/02* | (2006.01) |
| *A61K 8/97* | (2017.01) |
| *A61Q 19/08* | (2006.01) |
| *A61K 9/00* | (2006.01) |
| *A61K 47/10* | (2017.01) |
| *A61K 47/14* | (2017.01) |
| *A61K 47/32* | (2006.01) |
| *A61K 47/36* | (2006.01) |
| *A61K 9/10* | (2006.01) |
| *A61Q 19/00* | (2006.01) |
| *A61K 36/05* | (2006.01) |
| *A61K 36/28* | (2006.01) |
| *A61K 36/31* | (2006.01) |
| *A61K 36/45* | (2006.01) |
| *A61K 36/736* | (2006.01) |

(52) U.S. Cl.
CPC .............. *A61K 8/97* (2013.01); *A61K 8/975* (2013.01); *A61K 9/0014* (2013.01); *A61K 9/10* (2013.01); *A61K 36/05* (2013.01); *A61K 36/185* (2013.01); *A61K 36/28* (2013.01); *A61K 36/31* (2013.01); *A61K 36/45* (2013.01); *A61K 36/736* (2013.01); *A61K 47/10* (2013.01); *A61K 47/14* (2013.01); *A61K 47/32* (2013.01); *A61K 47/36* (2013.01); *A61Q 19/004* (2013.01); *A61Q 19/08* (2013.01); *A61K 2800/10* (2013.01); *A61K 2800/43* (2013.01); *A61K 2800/48* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 6,153,208 A | 11/2000 | McAtee et al. | |
| 6,214,322 B1 | 4/2001 | Castro et al. | |
| 6,406,682 B1 | 6/2002 | Martin et al. | |
| 6,723,667 B1 | 4/2004 | Saito et al. | |
| 8,206,721 B2 | 6/2012 | Stutz et al. | |
| 8,557,249 B2 | 10/2013 | Brooks et al. | |
| 2007/0122492 A1 | 5/2007 | Behr et al. | |
| 2008/0081085 A1 | 4/2008 | Mitra et al. | |
| 2009/0104295 A1 | 4/2009 | Kohno | |
| 2010/0285161 A1 | 11/2010 | Mitra et al. | |
| 2010/0285162 A1 | 11/2010 | Mitra et al. | |
| 2010/0316720 A1* | 12/2010 | Stutz et al. .................. | 424/486 |
| 2011/0250178 A1 | 10/2011 | Brooks et al. | |
| 2013/0287714 A1 | 10/2013 | Gohla et al. | |
| 2014/0170184 A1 | 6/2014 | Brooks et al. | |

FOREIGN PATENT DOCUMENTS

| | | |
|---|---|---|
| EP | 2260829 A2 | 12/2010 |
| ES | 2352403 B | 2/2011 |
| JP | H09136823 A | 5/1997 |
| JP | 2002114703 A | 4/2002 |
| JP | 2006104117 A | 4/2006 |
| JP | 2009185007 A | 8/2009 |
| KR | 20100067831 A1 | 6/2010 |
| KR | 20130053151 A | 5/2013 |
| WO | 2010054322 A1 | 5/2010 |
| WO | 2012069073 A1 | 5/2012 |

OTHER PUBLICATIONS

Streb et al. (1997) Plant, Cell and Environment 20, 1030-1040.*
Laureau et al. (2011) Physiologia Plantarum 143; 246-260.*
Kim et al. (2009) Eur. J. Phamacology 602: 148-156.*
Yvon, David (2012) The sun protection effect of glutathione. (available at http://www.articlesfactory.com/articles/health/the-sun-protection-effect-of-glutathione.html). Downloaded from website May 14, 2016.*
Shmakova et al. (2013) Botany Research International 6(3): 56-61.*
Hanada et al. (1991) J. Invest. Dermatol. 96:838-840.*
Streb, "Resistance to photoinhibition of photosystem II and catalase and antioxidative protection in high mountain plants", Plant Cell Environ., 1997, vol. 20, pp. 1030-1040.
List, "Hagers Handbuch der Pharmazeutischen Praxis" (Hagers Handbook of Pharmaceutical Practice, vol. 6. 4. edition, Berlin, Heidelberg, New York: Springer Verlag, 1979, p. 452.
Shang et al., "Slow turnover of the D1 reaction center protein of photosystem II in leaves of high mountain plants", FEBS Letters 425 (1998), pp. 97-100.
Yoon et al., "Anti-oxidant and Anti-aging Activity of Saxifraga stolonifera Meerburgh Ethanol Extract", Yakhak Hoeji Vo. 51, o. 5, pp. 343-349.

* cited by examiner

*Primary Examiner* — Chris R Tate
*Assistant Examiner* — Russell Fiebig
(74) *Attorney, Agent, or Firm* — Abel Law Group, LLP (57) ABSTRACT

Disclosed is a cosmetic or dermatological preparation which comprises one or more extracts of *Saxifraga oppositifolia* (purple saxifrage) and/or one or more extracts of *Soldanella alpina* (alpine snowbell). The use of these extracts to combat extrinsic and intrinsic skin aging is likewise described.

20 Claims, 9 Drawing Sheets

PREPARATION FOR PROTECTING AGAINST EXTRINSIC AND INTRINSIC SKIN AGING

CROSS-REFERENCE TO RELATED APPLICATIONS

The present application claims priority under 35 U.S.C. §119 of German Patent Application No. 10 2013 216 295.2, filed Aug. 16, 2013, the entire disclosure of which is expressly incorporated by reference herein.

BACKGROUND OF THE INVENTION

1. Field of the Invention

The present invention relates to a cosmetic or dermatological preparation comprising one or more extracts of *Saxifraga oppositifolia* (purple saxifrage) and/or *Soldanella alpina* (alpine snowbell), and to the use thereof to combat extrinsic and intrinsic skin aging.

2. Discussion of Background Information

Skin aging is the term used to refer to the complex biological process of the change in the skin associated with aging. A distinction is made here between intrinsic skin aging, caused by internal physiological and genetic factors, and extrinsic skin aging.

Extrinsic skin aging is attributed to external factors such as e.g. environmental factors such as UV light, chemical reagents, mechanical stress, cigarette smoke, stress or air pollution. Since UV radiation is the main cause of extrinsic skin aging, one also speaks of "photoaging".

The extrinsic factors lead for example to wrinkling, skin sagging, loss of elasticity and dry appearance of the skin.

Intrinsic skin aging, also called chronological skin aging, is caused by internal physiological and genetic factors and reflects degradation processes in the skin. These processes are primarily attributed to a reduced proliferation activity of the skin cells, a reduced synthesis of the matrix proteins and an increase in the expression of matrix-degrading enzymes.

Aged cells exhibit a resistance to apoptotic signals, which leads to the accumulation in the tissue of nonproliferating aged cells with altered gene expression pattern.

Skin aging often results in the formation of wrinkles and lines and the loss of elasticity and tone.

Skin aging and wrinkling can be decisively delayed by appropriate skin protection. In the prior art, a multitude of options are presented for this purpose from a healthy way of life ranging to cosmetic and dermatological preparations that can be applied topically.

*Saxifraga oppositifolia* is a plant which is preferentially found in the temperate parts of the world on open stony grassland and moraines at altitudes between 1600 and 4500 meters and which is therefore the highest-elevation flowering plant in Europe.

The evergreen leaves withstand temperatures down to −40° C. without damage. The leaves are opposite one another in small mat-forming rosettes and are reversed oval to elongated lanceolate and 2.5 to 5 mm in length.

U.S. Pat. No. 6,406,682 B1, the entire disclosure of which is incorporated by reference herein, describes the plant genus *Saxifraga* as a constituent in or as self-tanning preparation.

*Soldanella alpina* is a plant of the Primulaceae. A preferred site is semishade on wet soils. The leaves are roundish and evergreen.

US 2009/0104295 A1, the entire disclosure of which is incorporated by reference herein, lists *Soldanella alpina* as one possible source of an active ingredient group as addition to the base hair growth complex.

It is desirable to provide preparations which are effective against extrinsic and intrinsic skin aging.

SUMMARY OF THE INVENTION

The present invention provides a cosmetic or dermatological preparation which comprises (i) one or more extracts of *Saxifraga oppositifolia* (purple saxifrage) and/or (ii) one or more extracts of *Soldanella alpina* (alpine snowbell).

In one aspect, at least one extract of *Saxifraga oppositifolia* and at least one extract of *Soldanella alpina* may be present in the preparation.

In another aspect, the preparation may comprise only one extract of *Saxifraga oppositifolia* and only one extract of *Soldanella alpina*, in particular only these two extracts and no further plant extracts.

In yet another aspect, the preparation may comprise either only one or more extracts of *Saxifraga oppositifolia* or only one or more extracts of *Soldanella alpina*. In particular, the preparation may in this case comprise only these one or more extracts and no further plant extracts.

In a still further aspect, the preparation according to the invention may additionally comprise one or more extracts of the genus *Chlamydomonas* (also called *Chlamydocapsa* sp. (snow algae)).

The entire disclosure of WO 2012/069073 A1 is hereby expressly incorporated by reference herein.

For example, the preparation according to the present invention may comprise one or more extracts of *Saxifraga oppositifolia*, one or more extracts of *Soldanella alpina* and one or more extracts of *Chlamydomonas* sp., meaning that in each case one or more extracts of all three plants are present in the preparation according to the invention and, as a result of their skin protection effects, can delay or even stop the extrinsic and intrinsic skin aging process.

The extracts present in the preparation according to the invention may be oil- or water-soluble extracts of *Saxifraga oppositifolia* and *Soldanella alpina*. Extracts of this type can be produced by, for example, the following or similar processes.

Plant Material:

The biomass of the plants is obtained by cultivating these plants in greenhouses or in the open air. The plants can either be cultivated by seeds (*Soldanella*) or multiplied by seedlings (*Saxifraga*) by planting them into appropriate soils. As soon as adult plants are available, mother plants can be divided to give smaller daughter plants. The plant material is harvested as maximal biomass in early summer. In order to ensure sustainable cultivation and to avoid destroying the plants, preferably only plant parts above the ground and particularly preferably only branches (stems) and/or leaves of the plants are utilized although, for example, flowers can likewise (in particular additionally) likewise be used.

The plant parts above the ground are cut and then dried as thoroughly as possible, for example in a suitable oven by means of warm circulating air or in a vacuum drying cabinet. The drying temperature is preferably between 40 and 45° C. in order to thermally stress the temperature-sensitive natural products as little as possible.

As a result of the drying, the moisture content of the material is reduced to preferably less than 10%. The dried material is then for example cut in a shredder in order to reduce its size to preferably a few millimeters. The material should then be stored in a cool and dry place until further processing.

Oil-soluble Products:

The production of oil-soluble extracts can take place for example by means of supercritical extraction with carbon dioxide (Supercritical Fluid Extraction, SFE). Here, SFE with carbon dioxide is used to extract oil-soluble active ingredients from the dried plant material. The extraction container is filled with the dried plant material and the material is compacted in order to eliminate air channels. The pressure of the gas is for example up to about 200 bar at a temperature of about 40° C. Under these conditions, the dynamic extraction is usually carried out for about 60 minutes. Then, the supercritical carbon dioxide is decompressed and returned and the lipophilic extract is collected in a collecting container. The extracts of several runs are combined and dissolved for example in a corresponding amount of plant oil (e.g. jojoba oil) by means of stirring for one hour at about 50° C. After cooling, the solution is passed through a 25 μm filter and a 4 μm filter. The filtered solution corresponds to the oil-soluble extract product. As a result, 1500 g of dried *Saxifraga* produce for example about 15 kg of product (the yield of the extraction is usually 5-10%), while 900 g of dried *Soldanella* produce about 15 kg of product (the yield of the extraction is usually 2-5%).

The extracted plant material can be collected and used for example for the hydro-alcoholic extraction described below.

Water-soluble Products:

1. Hydro-ethanolic Extraction

The plant material is mixed with an adequate amount of water and ethanol (1:1 w/w). The slurry is stirred at room temperature for about 24 hours and then passed through a 1 μm filter. The solvated plant material can be squeezed in order to obtain further extract. The filtrate is diluted with approximately 1.5 times the weight of water and then stored at 4° C. for several days. The product is then passed through a 4 μm filter and a 0.6 μm filter and then subjected to a spray granulation.

2. Spray Granulation

The extraction solution is admixed with maltodextrin before the spray granulation. For example, about 100 kg of spray granules are produced with 10 kg of the dried (<10% water content) and cut *Saxifraga* raw material, and about 100 kg of spray granules are produced with 6 kg of the dried and cut *Soldanella* raw material.

The solution admixed with maltodextrin can be spray-granulated in a fluidized-bed granulating device, for example under the following conditions:

Granulation:
Incoming air: 80° C./250 to 800 m³/h
Spray rate: 3 bar/150-200 ml
Exiting air: 30-50° C.
Drying:
Incoming air: 80° C./250 to 800 m³/h/5-10 minutes
Exiting air: 55° C.
Period: several hours, depending on batch size.

The above production processes, given merely by way of example, are the preferred forms of providing the water- or oil-soluble extracts *Saxifraga oppositifolia* and *Soldanella alpina* for use according to the invention of. As mentioned above, in particular only the leaves and plant stems are used advantageously here, but no flowers and no roots of the plants.

Since the extracts can be produced and used both in oil- and in water-soluble form, there is great freedom for formulating cosmetic and pharmaceutical preparations.

The extracts can be used in any desired concentration in cosmetic or dermatological preparations.

Preferably, the concentration of one or more extracts of a plant (*Saxifraga oppositifolia*, *Soldanella alpina* and any other plant whose extract(s) is or are optionally present in the preparation, such as for example of *Chlamydocapsa* sp.) in the preparation is, in each case independently, not more than 15% by weight, for example not more than 5% by weight, not more than 1% by weight, not more than 0.5% by weight, not more than 0.1% by weight, or not more than 0.01% by weight, but preferably at least 0.0001% by weight, for example at least 0.0005% by weight, at least 0.001% by weight, or at least 0.002% by weight. Usually, the corresponding concentration range for the extract(s) of any one plant is 0.0001 to 0.5% by weight, in each case based on the total mass of the preparation.

The above concentration data for the extracts used according to the invention refer to the mass of the pure (generally pulverulent) extract, without solvents or extractants.

The extracts used according to the invention are produced for example, in the form of the products AlpinEffect *Saxifraga* SFE OS (0.2% by weight dry extract, remainder jojoba oil), AlpinEffect *Saxifraga* WS (0.3% by weight dry extract, >91% by weight maltodextrin, remainder predominantly water), AlpinEffect *Soldanella* SFE OS (0.08% by weight dry extract, remainder jojoba oil) and AlpinEffect *Soldanella* WS (0.4% by weight dry extract, >91% by weight maltodextrin, remainder primarily water) by the company Mibelle (Switzerland). (OS=oil-soluble; WS=water-soluble).

If, for example, 1% by weight of AlpinEffect *Soldanella* WS is used in the preparation, then the fraction of actual *Soldanella alpina* extract in the preparation is about 0.004% by weight, based on the total mass of the preparation.

The preparations according to the invention can be present in, for example, the known forms and types. An example of a known form of the preparations is a leave-on preparation, such as, for example, as cream, lotion or body milk. These preparations are often formulated as emulsions, in particular W/O, O/W, O/W/O or W/O/W emulsions. The preparations can likewise be microemulsions, dispersions, gels, aqueous or alcoholic solutions, sera, oils, wipe impregnation media, tinctures, ointments or salves. The extracts can advantageously also be applied to the skin in a form applied to or integrated in, e.g., wipes, plasters, bandages, patches or pads.

The cosmetic or dermatological preparations according to the invention can optionally comprise further active constituents. Merely by way of example, mention may be made here of further extracts such as, for example, one or more extracts of *Artemisia umbelliformis*, *Rubus idaeus* (raspberries), *Plantago lanceolata* (leaf extract), *Saccharomyces cerevisiae*, *Panax ginseng* root, *Equisetum arvense*, and *Evernia furfuracea* (tree moss). Further examples of preferred additional active constituents include biopolymers, glycoproteins, vitamins, amino acids and antioxidants.

The cosmetic or dermatological preparations according to the invention can also comprise auxiliaries and further active ingredients, as are usually used in such preparations, e.g. substances for preventing foaming, dyes and colored pigments, thickeners, moisturizing and/or humectant substances, fats, oils, waxes and other customary constituents of a cosmetic or dermatological formulation such as alcohols, polyols, polymers, foam stabilizers, electrolytes, organic solvents or silicone derivatives, provided their addition does not significantly impair the desired properties as regards the protective function and skin and hair compatibility.

According to the invention, one or more extracts of *Saxifraga oppositifolia* (purple saxifrage) and/or *Soldanella alpina* (alpine snowbell) can be used in cosmetic or dermatological preparations for reducing or avoiding skin damage by extrinsic and/or intrinsic factors, and can be used for producing pharmaceutical, in particular dermatological preparations and serve for reducing or avoiding skin damage by extrinsic and/or intrinsic factors.

The extracts according to the invention are preferably present in preparations that can be applied topically. In particular, the preparation that can be applied topically is a cosmetic preparation.

One or more extracts of *Saxifraga oppositifolia* and/or *Soldanella alpina* can thus also be used for producing pharmaceutical, in particular dermatological preparations.

Preferably, the extracts according to the invention are used in combination with one or more extracts of *Chlamydocapsa* sp. (snow algae).

To sum up, the present invention provides the following in particular:

1. A cosmetic or dermatological preparation which comprises (i) one or more extracts of *Saxifraga oppositifolia* and/or (ii) one or more extracts of *Soldanella alpina*.
2. The preparation of item 1, which comprises at least (i).
3. The preparation of item 1, which comprises at least (ii).
4. The preparation of item 1, which comprises both (i) and (ii).
5. The preparation of any of the preceding items, which comprises no additional plant extracts.
6. The preparation of any of the preceding items which, based on the total mass of the preparation, comprises not more than 15% by weight, e.g., not more than 5% by weight, or from 0.0001 to 0.5% by weight, of (i) and/or not more than 15% by weight, e.g., not more than 5% by weight, or from 0.0001 to 0.5% by weight of (ii).
7. The preparation of any of the preceding items, in which (i) and/or (ii) comprise at least one water-soluble extract and/or in which (i) and/or (ii) comprise at least one oil-soluble extract.
8. The preparation of any of the preceding items, in which all extracts (i) and/or (ii) are either water-soluble or oil-soluble.
9. The preparation of any of the preceding items, in which (i) and/or (ii) were obtained by extraction from plant leaves and/or plant stems.
10. The preparation of any of items 1-4 and 6-9, which additionally comprises (iii) one or more extracts of *Chlamydocapsa* sp.
11. The preparation of any of items 1-4 and 6-10, which additionally comprises at least one extract that is different from (i), (ii) and (iii).
12. The preparation of item 11, which additionally comprises one or more extracts selected from *Artemisia umbelliformis* extract, *Rubus idaeus* (raspberry) extract, *Plantago lanceolata* leaf extract, *Saccharomyces cerevisiae* extract, *Panax ginseng* root extract, *Equisetum arvense* extract, *Evernia furfuracea* (tree moss) extract.
13. The preparation of any of the preceding items, which additionally comprises at least one amino acid.
14. The preparation of any of the preceding items, which is present in the form of an emulsion.
15. The preparation of any of the preceding items, which is a topical preparation.
16. A method for reducing or avoiding skin damage by extrinsic and/or intrinsic factors, which comprises the topical application of a preparation of any of items 1 to 15 to the skin.
17. A method for delaying intrinsic and/or extrinsic skin aging, which comprises the topical application of a preparation of any of items 1 to 15 to the skin.
18. The use of one or more extracts of *Soldanella alpina* for producing pharmaceutical, in particular dermatological preparations.
19. The use of item 18, in which additionally at least one extract of *Saxifraga oppositifolia* and/or *Chlamydocapsa* sp. is used.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Hereinbelow, the advantageous properties of the preparation according to the invention are illustrated by reference to the results of various tests. In all of the tests, the aforementioned water-soluble extract products AlpinEffect *Saxifraga* WS and AlpinEffect *Soldanella* WS were used. The percentages refer to extract actually used (i.e. without the additives present in these products such as, for example, maltodextrin).

1. Mitochondrial Function Under Oxidative Stress

It is known that mitochondria are responsible for generating energy in human cells. They are located in the cytoplasm and serve the cells as "batteries", in order to produce, store and distribute energy. The human cell contains on average 1500 mitochondria. Cells with a high metabolic output (e.g. muscles or the liver) contain more mitochondria. The mitochondria move in the cytoplasm according to the demand of the cell. They are equipped with their own DNA and can therefore replicate independently irrespective of cell division. Without the mitochondria, the cell is incapable of functioning and no life is possible. If these powerhouses of the cells do not work correctly, this can accelerate aging processes in the skin. Defects in the mitochondria, in particular also in the mitochondrial DNA, can therefore accelerate aging.

Protection of the mitochondrial functionality against extrinsic disturbance factors, e.g. against UV radiation and oxidative stress, and/or the guarantee of the integrity of the mitochondria is therefore an effective protection against skin aging.

The following test shows that 10 mM hydrogen peroxide solution reduces the membrane potential of the mitochondria as a measure of healthy, metabolically active skin cells by about 50%. Hydrogen peroxide is therefore an example of extrinsic disturbance factors.

In the presence of both the *Saxifraga* and the *Soldanella* extract, the reduction in the membrane potential as a result of hydrogen peroxide is only about 25%, i.e. the extracts according to the invention protect the skin cells effectively against oxidative stress and therefore against extrinsic skin aging.

For carrying out the tests, primary human epidermal keratinocytes, more precisely "transit amplifying cells", were used.

In order to analyze the influence of the extract on mitochondrial functionality following oxidative stress, a JC-1 mitochondria membrane potential assay was carried out. In healthy cells, the metabolically active mitochondrial potential is high and the dye JC-1 spontaneously forms complexes (J aggregates) and as a result displays an intensive red fluorescence. On the other hand, the dye JC-1 remains in the uncomplexed, monomeric form in damaged cells with a low membrane potential. The ratio of the fluorescence intensity of J aggregates to JC-1 monomers serves as a measure for the functionality of the cell.

Figure 1:
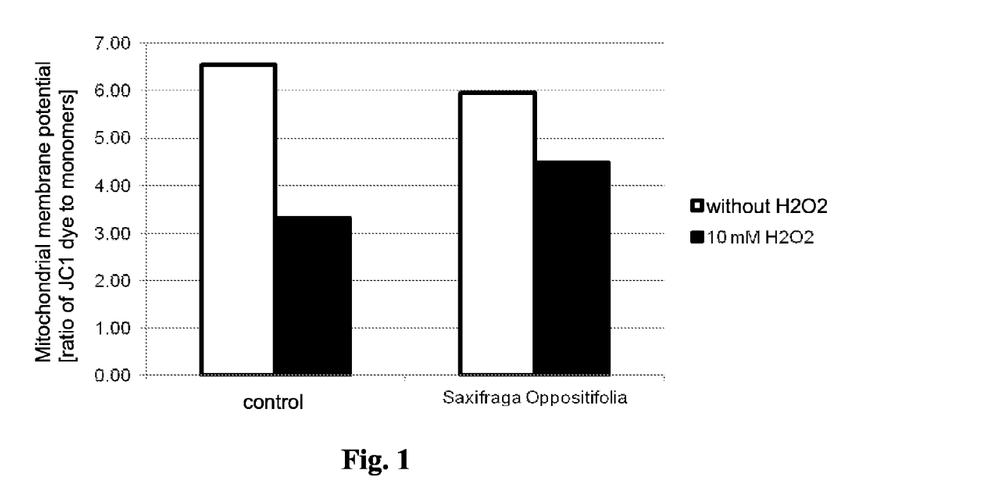
FIGS. 1 and 2 are bar diagrams which graphically represent the results set forth below under the heading Mitochondrial function under oxidative stress.
Figure 2:
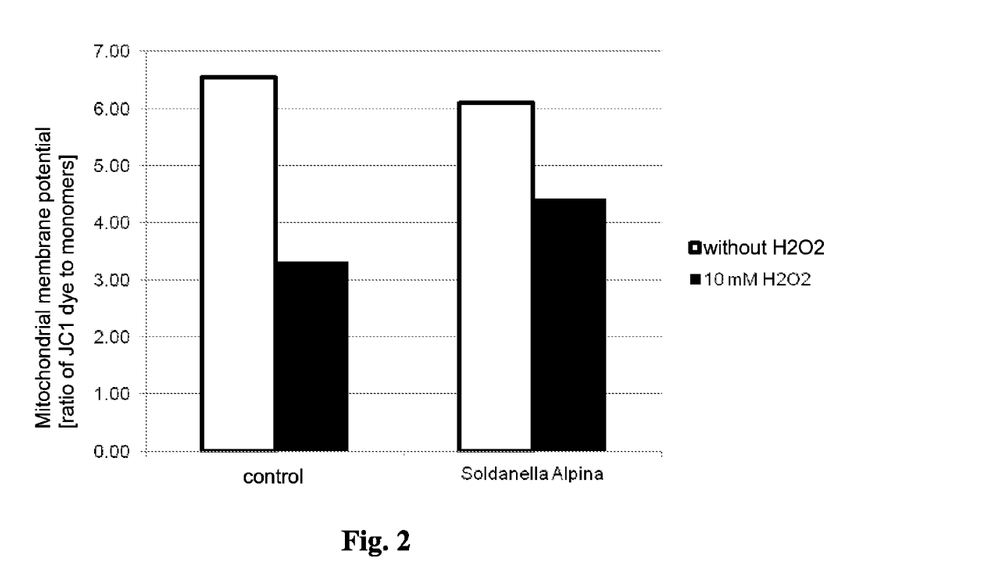

The test results are shown graphically in FIGS. 1 and 2. These Figures show the effectiveness and protective function of the extracts according to the invention against extrinsic disturbance factors.

The concentration of *Saxifraga oppositifolia* used in the test was 0.00024% by weight and that of *Soldanella alpina* was 0.00024% by weight (based on the weight of the cell medium).

2. Protection of Mitochondrial DNA Upon UV Irradiation

The following assay shows the protective effect of the extracts according to the invention as regards mitochondrial DNA upon UV irradiation.

Located on the mitochondrial DNA (mtDNA) are some, if not all, of the genes for the enzymes of the respiratory chain, as well as genes which are responsible for the structure and reproduction of the mitochondria. Damage to the mtDNA can arise very easily, it is present in unprotected form in the mitochondria and is exposed there to the free radicals which can be formed during the production of energy. Damage to the mtDNA can therefore lead to a severe impairment of cellular energy production.

One of the most frequent types of damage to the mtDNA, which is detected in the assay below, is referred to as "common deletion".

HaCaT cells are cells of a specific human keratinocyte cell line. Cultivated keratinocytes (HaCaT) are incubated for 48 h with various compounds and then stressed for 1 h with UVB radiation (1.5 mJ/cm$^2$). The cells are then collected and lyzed for the purposes of DNA extraction.

With the help of the intensity of the common deletion band, expressed as a ratio of the common deletion compared to standard, the protection against damage by UV light can be determined.

Figure 3A:
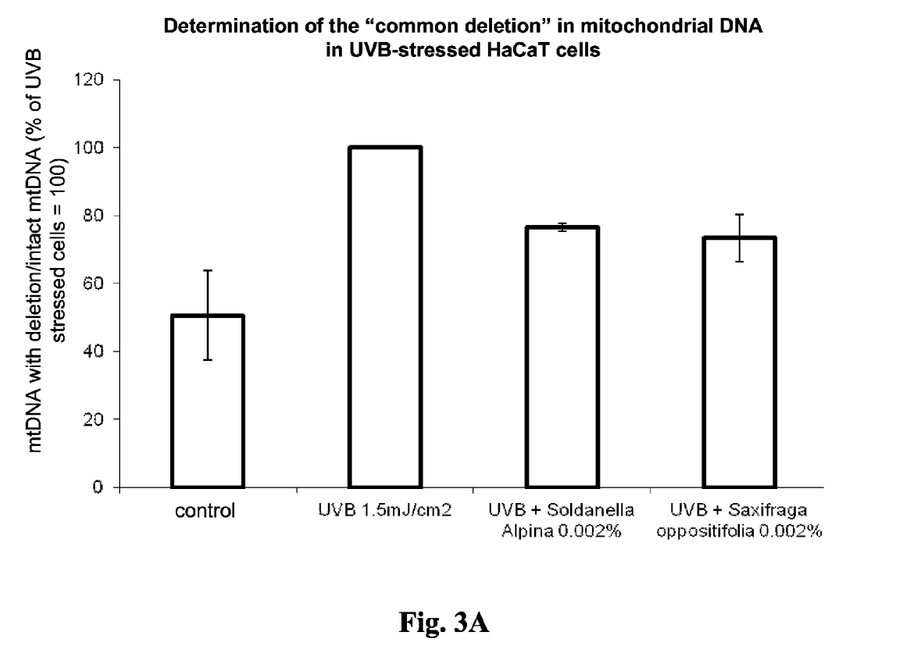
FIGS. 3A-3C are bar diagrams which graphically represent the results set forth below under the heading Protection of mitochondrial DNA upon UV irradiation.
Figure 3B:
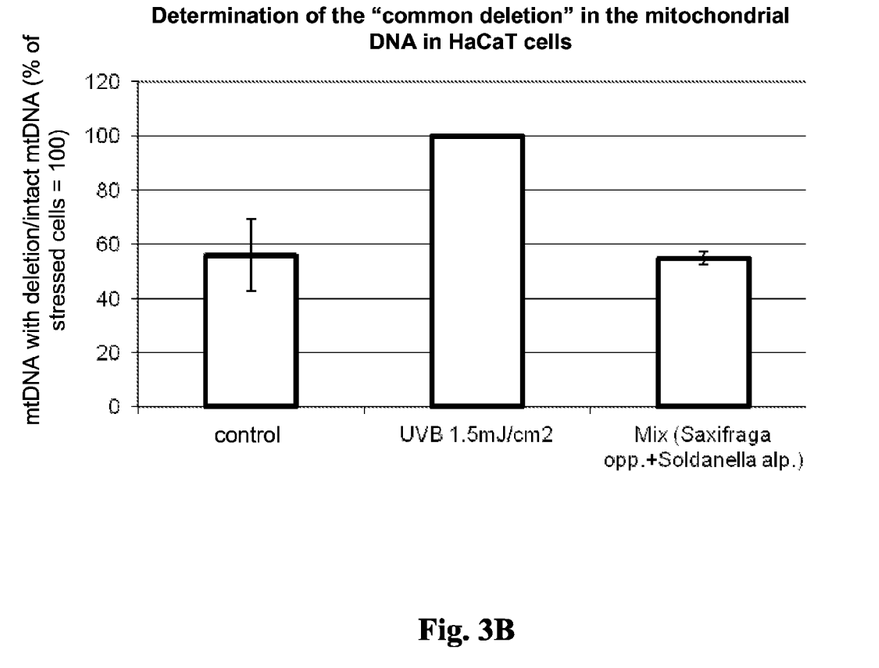
Figure 3C:
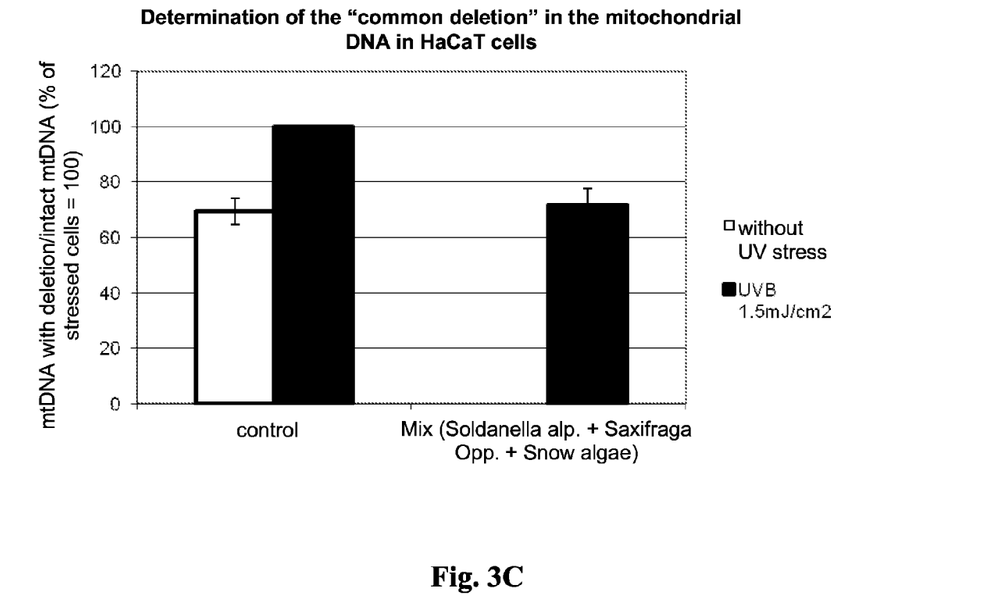

The following compounds were investigated:

| Plant extracts | Fraction % by wt. | % reduction in the DNA damage induced by UVB (common deletion test) | Figure |
|---|---|---|---|
| *Saxifraga oppositifolia* | 0.002% | −46% | 3A |
| *Soldanella alpina* | 0.002% | −52% | 3A |
| *Saxifraga* + *Soldanella* | *Saxifraga* = 0.0003% *Soldanella* = 0.00036% | −100% | 3B |
| *Saxifraga* + *Soldanella* + snow algae | *Saxifraga* = 0.00033% *Soldanella* = 0.0004% snow algae = 0.0022% | −92% | 3C |

FIG. 3A shows that *Soldanella alpina* extract reduces the UV-induced damage of the mitochondrial DNA in keratinocytes (HaCaT cells) by 52% and *Saxifraga oppositifolia* extract by 46% relative to the control.

The combination of the extracts of *Saxifraga oppositifolia* and *Soldanella alpina* reduces the UV-induced damage by 100% (FIG. 3B). Even at a fraction of 0.0003%-0.00036% of extracts used according to the invention, a significant protection is observed which, as FIG. 3B shows, can be increased to 100% upon increasing the concentration and combining the extracts.

The combination with a further preferably used algae or plant extract, *Chlamydomonas* (*Chlamydocapsa* sp. (snow algae)), also leads to an almost 100% protection against damage induced by UV radiation (FIG. 3C).

3. Protection of Cellular DNA Upon UV Irradiation

DNA damage leads to an impairment of cellular functions and ultimately to skin aging. UV radiation is the essential factor in the case of premature (extrinsic) skin aging.

3D epidermal cultures were investigated using primary human keratinocytes and 3D prime culture medium. After 18 days, the cultures were treated for 1 hour with 100 µl either of a solution of *Soldanella alpina* extract in medium or medium on its own (untreated controls). In the case of an irradiation of 1200 mJ/cm$^2$ (total UV), the samples were then exposed to 4 hours of UVB/UVA light (20%/80%). The samples were then fixed, embedded into paraffin, cut and stained with thymine dimers using a monoclonal antibody. Images were then recorded using a fluorescence microscope.

Result:

In the untreated control, no thymine dimers were observed. In UV-exposed controls, nuclear thymine dimers were clearly visible in the lower layers of the samples. In contrast to this, no dimers were visible in the cells treated with *Soldanella alpina* (0.1%) and UV-treated cells. This shows that the extract from *Soldanella alpina* prevents the formation of UV-induced DNA damage in the cells of an epidermal three-dimensional skin model and thus prevents extrinsic skin aging or photoaging.

4. Delaying the Aging Process of Human Keratinocytes (Intrinsic Skin Aging)

Besides the protective function against extrinsic factors, the extracts used according to the invention also exhibit an effectiveness as regards delaying the aging process of human keratinocytes (intrinsic skin aging).

In order to demonstrate this, human keratinocytes in an early growth phase (transit amplifying cells) were incubated in a defined medium, in which these cells age within four weeks, with and without *Soldanella* extract and the proliferation rate of the cells was determined as a measure of their aging.

In order to assess the intrinsic anti-aging function of the extracts, the cells were cultivated in CnT-07 medium (progenitor cell targeted medium) or in CnT-AG1 medium, a completely defined aging medium in which the keratinocytes age over a period of four weeks. The signs of aging include a reduction in the proliferation rate. The proliferation was measured every week using an automated cell counter. During the first two weeks of aging, the proliferation rates of the keratinocytes which have been treated with plant extracts were similar to those of the cells growing in the CnT-AG1 medium alone. After an aging process of 3 to 4 weeks, however, the differences increased. In the $4^{th}$ week, the proliferation rate of the cells with *Soldanella alpina* extract (0.00024%) compared to the CnT-AG1 control was more than 40% higher.

Figure 4:
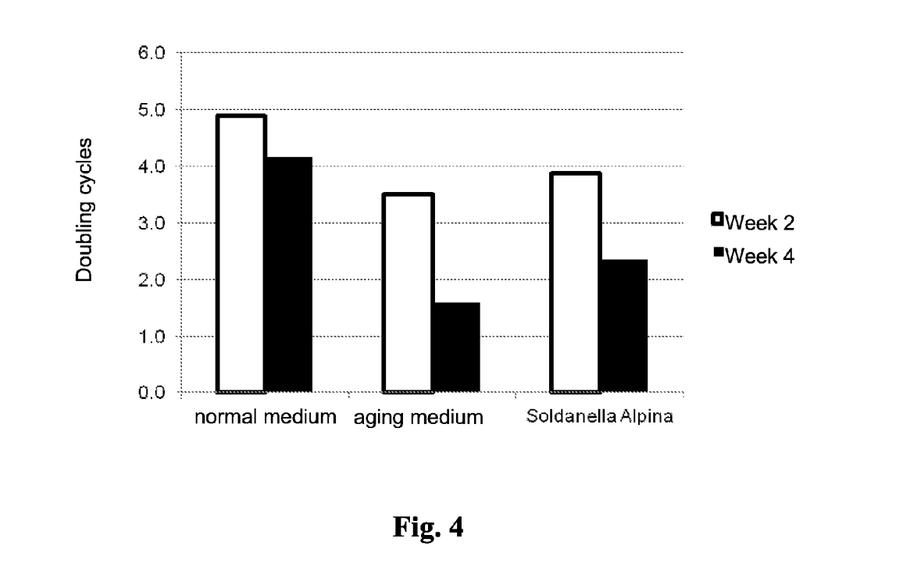
FIG. 4 is a bar diagram which graphically represents the results set forth below under the heading Delaying the aging process of human keratinocytes (intrinsic skin aging)

FIG. 4 shows that the proliferation of the cells in the aging medium in the presence of the *Soldanella alpina* extract after 2 and 4 weeks is higher than in the aging medium without extract. Since aged cells no longer replicate as quickly and thus have a lower proliferation rate than young cells, this shows that the intrinsic aging of the cells is slowed by the *Soldanella alpina* extract.

5. Formation of Epidermal Skin Following UV Irradiation

The new formation of epidermal skin is also destroyed by UV irradiation.

The renewing of the epidermis is ensured by the epidermal stem cells and their direct descendants, the "transit amplifying cells". If these cells lose their ability for skin renewal, be it through aging or as a result of external stress, e.g. UV radiation, then skin renewal in general slows and the quality, that is to say the thickness of the epidermis, reduces and signs of skin aging become visible.

Figure 5:
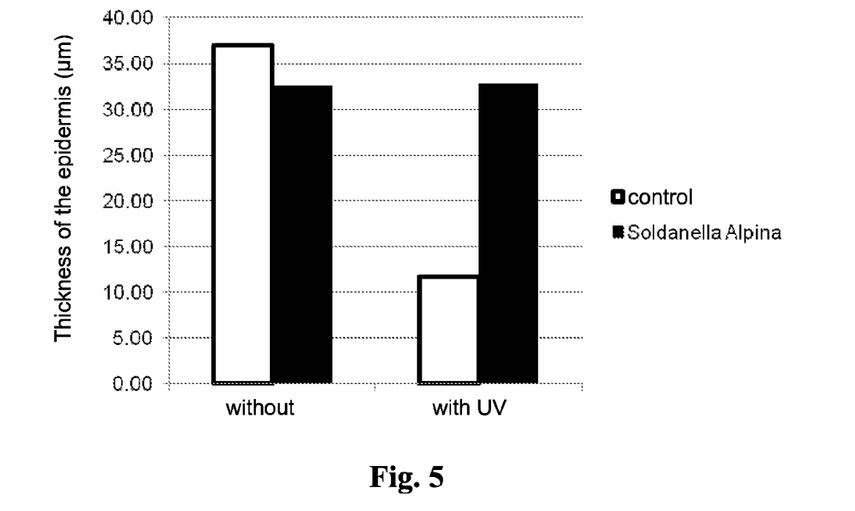
FIGS. 5 and 6 are bar diagrams which graphically represent the results set forth below under the heading Formation of epidermal skin following UV irradiation.
Figure 6:
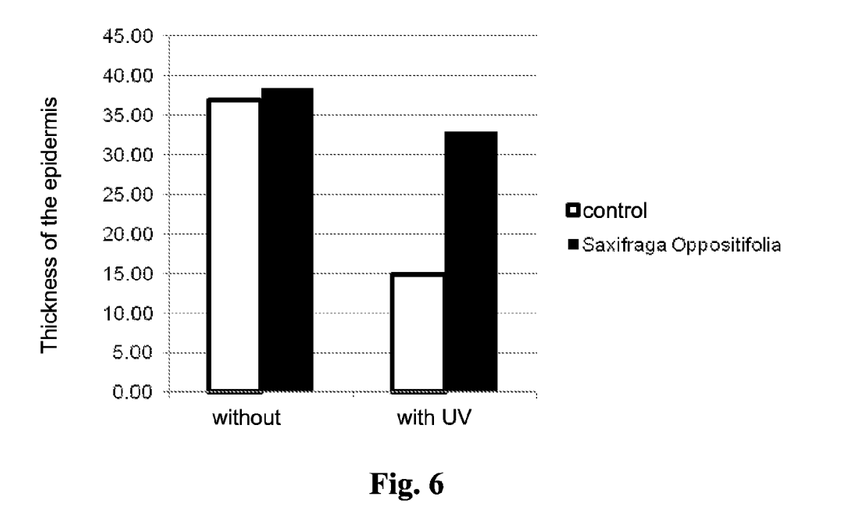

Test Design:

An important indicator of the keratinocyte progenitor cells function is the possibility to form a coated, 3D epidermal structure. In order to assess the ability of the plant extracts used according to the invention to protect against the loss of the progenitor cells function, keratinocytes were left to grow to 80% confluence in culture medium and then treated for 24 hours with 0.002% *Soldanella alpina* extract or with 0.002% *Saxifraga oppositifolia* extract. The cells were then subjected to UVB/UVA light. Unilluminated samples served as a negative control. One hour after the UV treatment, the cells were sown out for the construction of 3D models using the standard protocol. On the $18^{th}$ day of the airlift culture, 3D model samples were taken, embedded into formalin, fixed into paraffin, cut and stained. Histological cuts were then evaluated under the light microscope. Duplicate images were taken and for each position, the epidermal thickness (from the basal layer down to the horny layer) was measured. The result found was that both extracts used according to the invention conserve the skin renewal potential of human skin cells under UV stress. Without pretreatment of the skin cells with one of the two extracts, the cells lose their ability to form in vitro an intact three-dimensional epidermis if they are subjected to UV radiation. The extracts therefore protect the ability of the "transit amplifying cells" for skin renewal under UV stress. The epidermal thickness of the skin is retained, as shown in FIGS. 5 and 6.

6. Activation of the Proteasome in HaCaT Cells Following UV Stress

In a further assay, the activation of the proteasome in HaCaT cells following UV stress was investigated.

The proteasome is a protein complex which degrades in the cytoplasm and in the cell core (in the case of eukaryotes) proteins that are defective and no longer required to give fragments. The proteasome is therefore a constituent of protein quality control.

UV stress inhibits the proteolytic activity of the proteasome, which leads to the accumulation of proteins that are defective and/or no longer required and ultimately impairs cellular functions. If defective or oxidized proteins aggregate, this can lead to the formation of the aging pigment lipofuscin.

Figure 7:
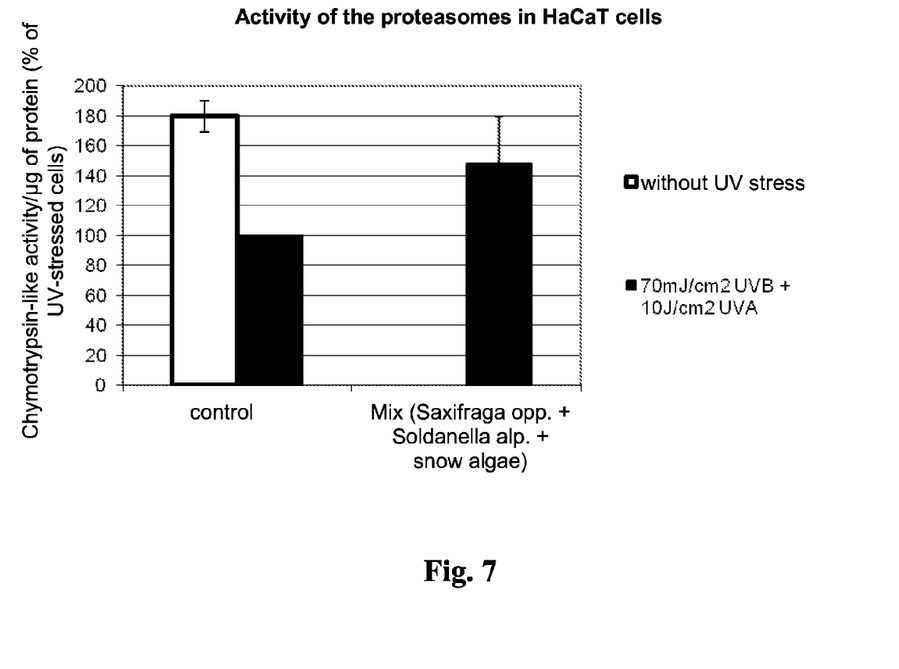
FIG. 7 is a bar diagram which graphically represents the results set forth below under the heading Activation of the proteasome in HaCaT cells following UV stress.

FIG. 7 shows the results following the treatment of the proteasomes with the combination according to the invention of three plant extracts (*Saxifraga oppositifolia*, *Soldanella alpina* and *Chlamydocapsa* sp.): the activity of the proteasomes in HaCaT cells following UV irradiation (70 mJ/cm$^2$ UVB +10 J/cm$^2$ UVA) is again increased or reactivated, and specifically by 48%.

The concentrations (% by weight) of the extracts were: *Saxifraga* 0.00033%, *Soldanella* 0.00044% and *Chlamydocapsa* 0.0022%.

7. Inhibition of the Release of the Matrix Metalloproteinases MMP-1 and MMP-3 Following UVA Stress in Human Dermal Fibroblasts Further tests were carried out as regards the inhibition of the release of the matrix metalloproteinases MMP-1 and MMP-3 following UVA stress in human dermal fibroblasts.

Matrix metalloproteinases are proteases which degrade components of the extracellular matrix. UV light can stimulate the expression of matrix metalloproteinases.

MMP-1 is a collagenase, i.e. a collagen-degrading proteinase. Besides various collagens, MMP-3 also degrades fibronectin, elastin and laminin and plays a central role in the modulation of connective tissue and in wound healing.

Figure 8A:
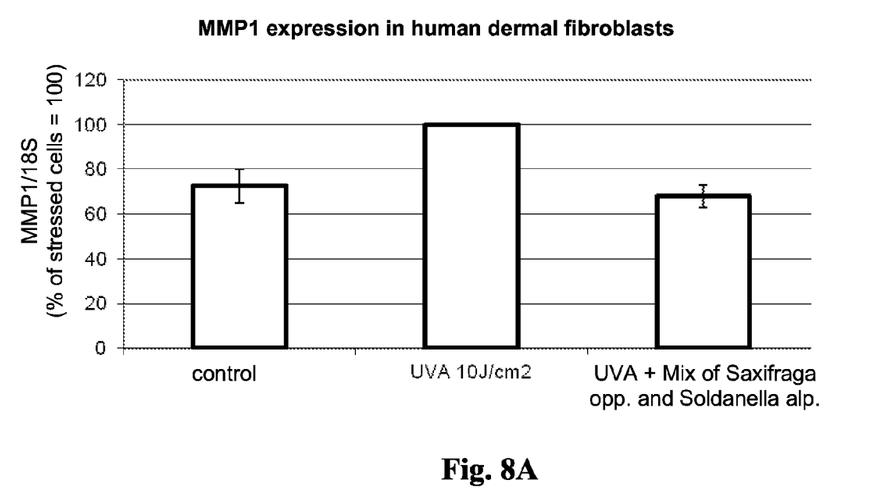
FIGS. 8A, 8B are bar diagrams which graphically represent the results set forth below under the heading Inhibiting the release of the matrix metalloproteinases MMP-1 and MMP-3 following UVA stress in human dermal fibroblasts.
Figure 8B:
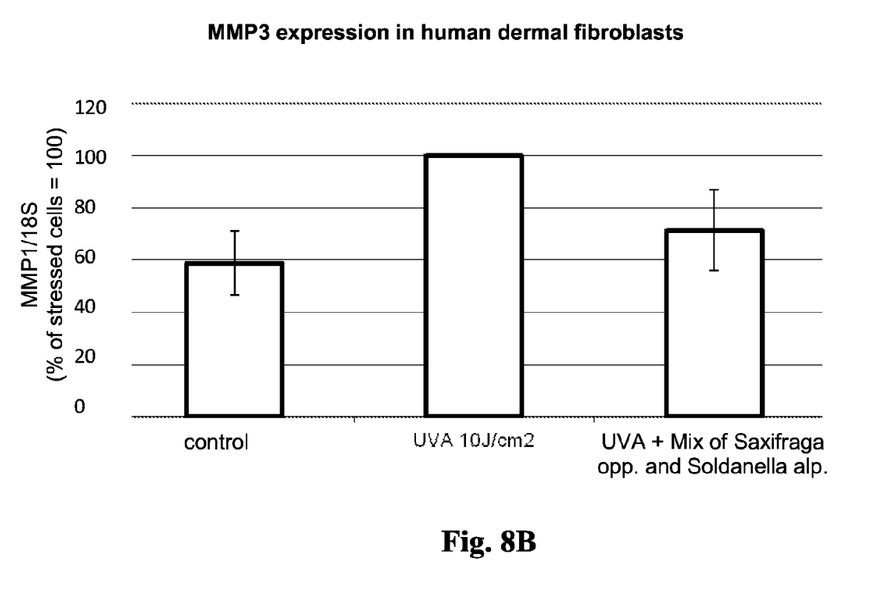

A preparation according to the invention which comprises a combination of extracts of *Saxifraga oppositifolia* (0.00135%) and *Soldanella alpina* (0.0018%) inhibits the UV-induced expression of MMP-1 and MMP-3 significantly and as a result prevents light-induced skin aging, as is evident from FIGS. 8A and 8B.

8. Colony Formation by Primary Epidermal Keratinocyte Precursor Cells Following UV Irradiation or Treatment with Hydrogen Peroxide The combination according to the invention of the extracts of *Saxifraga oppositifolia*, *Soldanella alpina* and *Chlamydomonas* sp. protects the proliferation potential of epidermal stem cells under UV and oxidative stress, as measured by the ability of the cells to form colonies in vitro (Colony Forming Efficiency=CFE). For this, the following experiments were carried out:

UV Irradiation:

Primary epidermal keratinocyte precursor cells were sown out in the presence of the extract combination in CnT-07 culture medium and left to grow for 48 hours. Each sample is then subjected to an irradiation with a UVA and UVB light source (1200 mJ or 1800 mJ). A test with nonirradiated sample was likewise carried out. After the illumination, the cells for the CFE assays were sown out with a low density and cultivated. The cultures are then fixed and stained and the colonies were counted. The CFE evaluations were carried out three times. Untreated cells were used as control.

Hydrogen Peroxide:

Using a similar experimental design to that described for the UV irradiation, the CFE upon peroxide exposure was evaluated.

Figure 9A:
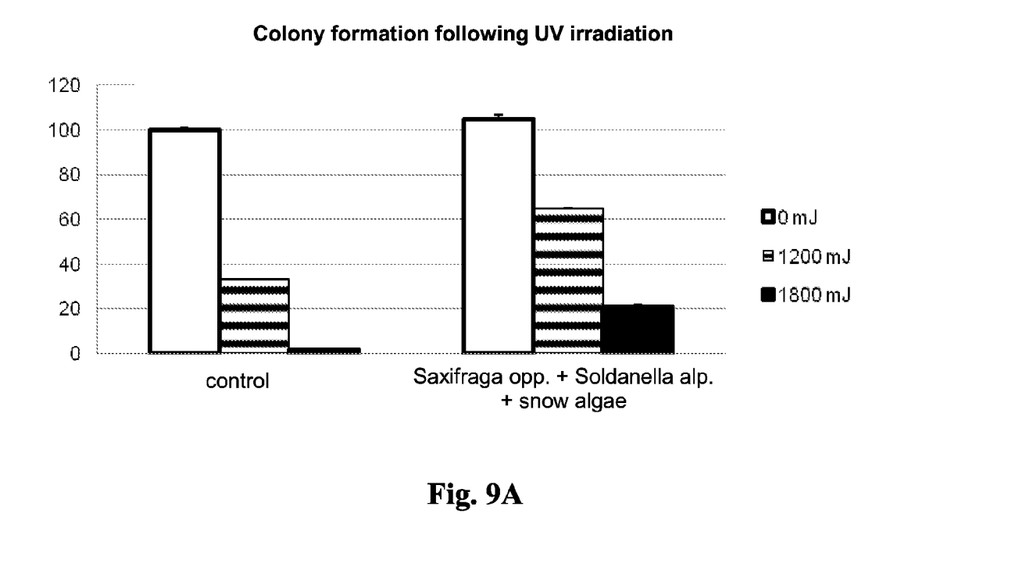
FIGS. 9A, 9B are bar diagrams which graphically represent the results set forth below under the heading Colony formation by primary epidermal keratinocyte precursor cells following UV irradiation or treatment with hydrogen peroxide.
Figure 9B:
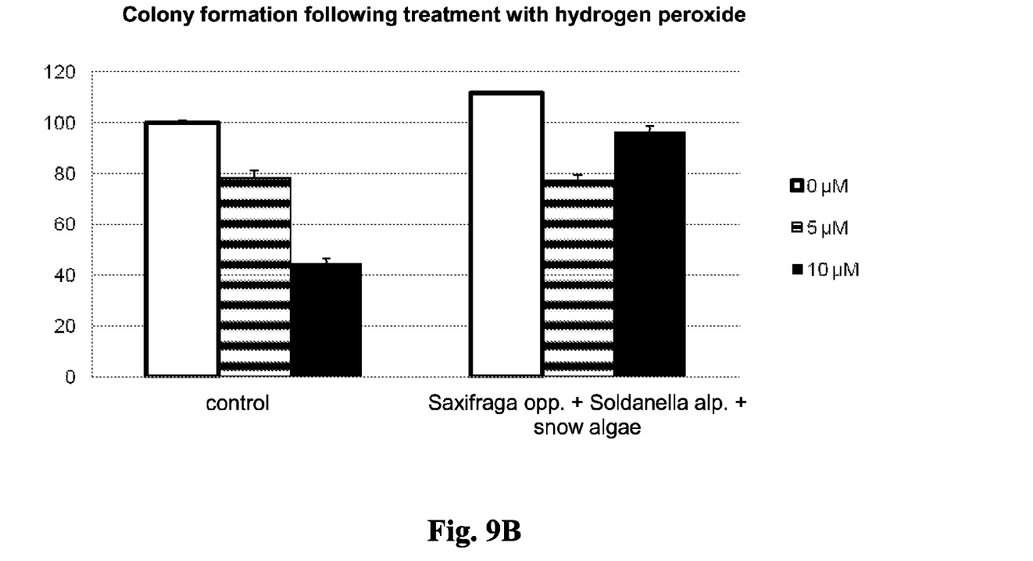

As the results depicted graphically in FIG. 9A show, the extract combination used according to the invention protects the proliferation potential of the epidermal stem cells significantly against UV radiation. For example, the number of colonies formed doubles in the presence of the extracts compared to the untreated control at 1200 mJ/cm$^2$. Likewise, the extracts protect against the negative influences of peroxides (10 µM) on the proliferation ability of the epidermal stem cells (FIG. 9B).

9. Formation of Spherical Colonies by Dermal Precursor Cells Following UV Irradiation The plant extracts used according to the invention protect not only epidermal, but also dermal stem cells against the negative effects of UV radiation on their proliferation ability.

Dermal precursor cells (isolated from dermal papilla) were cultivated in monolayers in the presence or absence of the extracts for a period of 2 days and then irradiated with a UVA and UVB light source with a dose of 1200 mJ or 1800 mJ. The formation of spherical colonies was evaluated after about 5 days of the cultivation.

Figure 10:
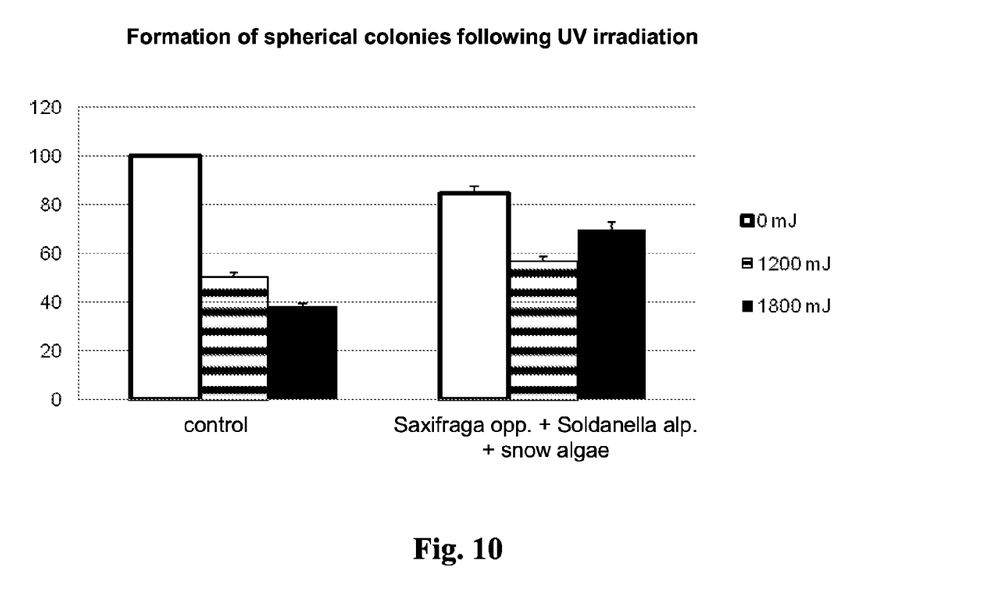
FIG. 10 is a bar diagram which graphically represents the results set forth below under the heading Formation of spherical colonies by dermal precursor cells following UV irradiation.

The proliferation ability of the dermal stem cells was ascertained by reference to their ability to form spherical colonies (spheres). Whereas in the control (without extracts) the number of spheres formed under UV irradiation (1200 mJ or 1800 mJ) dropped by 50% and 62%, respectively, the number of spheres in the presence of the extracts increased by up to 100% (FIG. 10).

Epidermal and dermal stem cells and their descendants are essentially involved in the routine maintenance and renewal of the corresponding skin layer. The protection of these cells against external stressors such as UV radiation or free radicals therefore contributes significantly to the retention of youthful, healthy and beautiful skin.

The following non-limiting examples are intended to further illustrate the present invention.

EXAMPLE 1

| Care oil-containing preparation | |
|---|---|
| INCI | % by wt. |
| PRUNUS AMYGDALUS DULCIS (SWEET ALMOND) OIL | 91.0370 |
| HELIANTHUS ANNUUS (SUNFLOWER) SEED OIL | 4.0000 |
| SIMMONDSIA CHINENSIS (JOJOBA) SEED OIL | 1.1000 |
| SILYBUM MARIANUM ETHYL ESTER | 1.0000 |
| FRAGRANCE (PERFUME) | 1.5000 |
| PHENOXYETHANOL | 0.6000 |
| CAPRYLIC/CAPRIC TRIGLYCERIDE | 0.5000 |
| TOCOPHERYL ACETATE | 0.1000 |
| C10-18 TRIGLYCERIDES | 0.0995 |
| BRASSICA CAMPESTRIS (RAPESEED) SEED OIL | 0.0495 |
| ALGAE EXTRACT | 0.0100 |
| SAXIFRAGA OPPOSITIFOLIA EXTRACT | 0.0040 |
| SOLDANELLA ALPINA EXTRACT | 0.0016 |
| | 100.0000 |

The preparation can advantageously be supplemented with further plant oils, oil-soluble vitamins and/or antioxidants.

EXAMPLE 2

| W/O emulsion | |
|---|---|
| INCI | % by wt. |
| WATER (AQUA) | 42.400 |
| GLYCERIN | 15.170 |
| CAPRYLIC/CAPRIC TRIGLYCERIDE | 10.500 |
| BUTYLENE GLYCOL | 6.150 |
| COCO-CAPRYLATE/CAPRATE | 4.000 |
| CYCLOPENTASILOXANE | 3.500 |
| DIMETHICONE | 3.000 |
| GLYCERYL STEARATE | 2.000 |
| CETYL ALCOHOL | 2.000 |
| MALTODEXTRIN | 1.900 |
| PEG-40 STEARATE | 1.800 |
| POTASSIUM CETYL PHOSPHATE | 1.600 |
| BUTYROSPERMUM PARKII (SHEA BUTTER) | 1.500 |
| PHENOXYETHANOL | 0.900 |
| SORBITAN TRISTEARATE | 0.700 |
| CARBOMER | 0.500 |
| FRAGRANCE (PERFUME) | 0.350 |
| CALCIUM ALUMINUM BOROSILICATE | 0.338 |
| ETHYLHEXYLGLYCERIN | 0.300 |
| SODIUM ACRYLATE/SODIUM ACRYLOYLDIMETHYL TAURATE COPOLYMER | 0.247 |
| PROPANEDIOL | 0.200 |
| SODIUM HYDROXIDE | 0.176 |
| ISOHEXADECANE | 0.163 |
| PENTYLENE GLYCOL | 0.150 |
| TITANIUM DIOXIDE | 0.135 |
| ISOMALT | 0.092 |
| SODIUM HYALURONATE | 0.070 |
| TRITICUM VULGARE (WHEAT) FLOUR LIPIDS | 0.050 |
| POLYSORBATE 80 | 0.046 |
| PEG-8 | 0.025 |
| SILICA | 0.023 |
| CHLAMYDOMONAS EXTRACT | 0.006 |
| SOLDANELLA ALPINA EXTRACT | 0.004 |
| SAXIFRAGA OPPOSITIFOLIA EXTRACT | 0.003 |
| CITRIC ACID | 0.002 |
| POTASSIUM SORBATE | 0.001 |
| | 100.000 |

This preparation can advantageously additionally comprise one or more of the following exemplary components:

Cellular Complex (La Prairie, Switzerland), peptides, plant extracts, extracts of plant stem cells, biopolymers, vitamins, antioxidants.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological preparation, wherein the preparation is in the form of an emulsion or a microemulsion, and wherein the preparation comprises, based on a total weight of the preparation, from 0.0001% to 15% by weight of one or more extracts of Soldanella alpine, in combination with one or more components selected from fats, oils, waxes, moisturizing and/or humectant substances, alcohols, polyols, polymers, electrolytes, organic solvents, silicones, foam stabilizers, substances for preventing foaming, dyes, coloring pigments, and thickeners.

2. The preparation of claim 1, wherein the preparation further comprises from 0.0001% to 15% by weight of one or more extracts of *Saxifraga oppositifolia*.

3. The preparation of claim 2, wherein the preparation comprises from 0.0001% to 1% by weight of the one or more extracts of *Soldanella alpine* and/or from 0.0001% to 1% by weight of the one or more extracts of *Saxifraga oppositifolia*.

4. The preparation of claim 1, wherein the one or more extracts of *Soldanella alpina* comprise at least one water-soluble extract obtained by hydro-alcoholic extraction of plant material.

5. The preparation of claim 4, wherein the *Soldanella alpina* plant material comprises plant leaves and/or plant stems.

6. The preparation of claim 1, wherein the one or more extracts of *Soldanella alpina* comprise at least one oil-soluble extract obtained by supercritical fluid extraction of plant material.

7. The preparation of claim 6, wherein the *Soldanella alpina* plant material comprises plant leaves and/or plant stems.

8. The preparation of claim 1, wherein the one or more extracts of *Soldanella alpina* are water-soluble.

9. The preparation of claim 1, wherein the preparation further comprises one or more extracts of *Chlamydocapsa* sp.

10. The preparation of claim 1, wherein the preparation further comprises one or more extracts of *Chlamydocapsa* sp.

11. The preparation of claim 1, wherein the preparation further comprises one or more extracts selected from *Artemisia umbelliformis* extract, *Rubus idaeus* (raspberry) extract, *Plantago lanceolata* leaf extract, *Saccharomyces cerevisiae* extract, *Equisetum arvense* extract, and *Evernia furfuracea* (tree moss) extract.

12. The preparation of claim 1, wherein the preparation is in the form of an emulsion.

13. The preparation of claim 1, wherein at least one extract of the one or more extracts of *Soldanella alpina* is oil-soluble, and the preparation comprises jojoba oil.

14. The preparation of claim 1, wherein at least one extract of the one or more extracts of *Soldanella alpina* is water-soluble, and the preparation comprises maltodextrin.

15. The preparation of claim 1, wherein the preparation is in the form of a microemulsion.

16. The preparation of claim 1, in which all of the one or more extracts of *Soldanella alpina* are oil-soluble.

17. The preparation of claim 2, wherein the preparation is in the form of an emulsion.

18. The preparation of claim 4, wherein the preparation is in the form of an emulsion.

19. The preparation of claim 6, wherein the preparation is in the form of an emulsion.

20. The preparation of claim 9, wherein the preparation is in the form of an emulsion.

* * * * *